United States Patent
Poreh et al.

(10) Patent No.: US 7,267,440 B2
(45) Date of Patent: Sep. 11, 2007

(54) METHOD FOR RECORDING, ASSESSING AND PREMEDITATING PERFORMANCE ON GRAPHO-MOTOR AND WRITING TASKS

(76) Inventors: Amir M. Poreh, 5178 Cheswick Dr., Solon, OH (US) 44139; Michael Poreh, 25 Eistein St., Haifa (IL)

(*) Notice: Subject to any disclaimer, the term of this patent is extended or adjusted under 35 U.S.C. 154(b) by 82 days.

(21) Appl. No.: 11/342,222

(22) Filed: Jan. 30, 2006

(65) Prior Publication Data
US 2006/0189903 A1     Aug. 24, 2006

Related U.S. Application Data

(60) Provisional application No. 60/648,695, filed on Feb. 2, 2005.

(51) Int. Cl.
*A61B 3/02* (2006.01)
(52) U.S. Cl. .................. 351/223; 351/238; 351/246

(58) Field of Classification Search ............. 351/222, 351/223, 237–239, 246
See application file for complete search history.

(56) References Cited

U.S. PATENT DOCUMENTS

| | | | |
|---|---|---|---|
| 2,663,218 A * | 12/1953 | Ranseen | 351/237 |
| 7,211,050 B1 * | 5/2007 | Caplygin | 600/558 |
| 2005/0196734 A1 * | 9/2005 | Poreh | 434/236 |

* cited by examiner

*Primary Examiner*—Huy Mai

(57) ABSTRACT

A computerized method for recording and scoring the process by which an examinee performs cognitive or psychological grapho-motor tasks that call for the use of pencil and paper, such as drawing or copying graphical configurations or text. The examinee uses a digital pen that leaves a trace on a writing pad. The trace is digitized in real time, input to a computer and stored in memory as a time dependent image. The image may be displayed and scored in real time or at a later stage on a computer display. The examiner can easily replay and reevaluate the graph-motor task process at a later stage.

13 Claims, 2 Drawing Sheets

METHOD FOR RECORDING, ASSESSING AND PREMEDITATING PERFORMANCE ON GRAPHO-MOTOR AND WRITING TASKS

CROSS REFERENCE TO RELATED APPLICATIONS

This application claims the benefit from U.S. provisional application 60/648,695 filed 2 Feb. 2005 by the present inventors.

FIELD AND BACKGROUND OF THE INVENTION

The present invention relates to the field of psychological testing and more specifically to cognitive assessment of head injured patients, patients with neurological disorders, individuals suffering from psychiatric illnesses, and adults or children with learning disabilities. The present invention relates particularly to tests and tasks for assessment, training and remediation of grapho-motor abilities that according to the present art the examinee performs such tasks using conventional writing and drawing elements such as paper, pencils, pens, markers.

Various psychological tasks have been developed for both diagnosis and remediation of skills required for performing grapho-motor tasks. In some common tasks the examinee is asked to copy simple or complex geometric figures or designs. Typical examples are the Rey Osterrieth Complex Figure[1], the Clock Drawing Test[2], the Army Tests[3], and the Bender-Gestalt Visual Motor Test[4], which are described in references 1 to 4, respectively. Some Mental Status Exams and the Wechsler Memory Scale[5] also include tasks of copying simple geometric figures or designs. In many other tasks, examinees are asked to copy letters, words and short sentences. In the art, evaluation of the performance of the examinee is most often based on evaluating the end result of the tasks, that is, on how accurately the examinee was able to accomplish the task[1, 2, 3, 4, 5, 6] in entirety. However, it is known that the process of copying complex figures or handwriting is also of considerable importance. The strategy, e.g. order, the examinee uses to accomplish a given complex task, and the way the examinee writes letters and sentences, are indicative of his cognitive abilities, learning deficits, and the source of his disabilities. Thus, various attempts to assess the process of performing tasks have been made. See reviews in references 7, 8, 9 and 21. These reviews indicate that initially, attention was focused on assessment of the qualitative features of the performance of tasks. Only recently, the significance and advantages of using what has been termed a Quantified Process Approach for characterizing and assessing the performance process became clear[10, 11, 12, 13, 14].

It is also important to realize that methods for recording the process by which an examinee accomplishes a task should not affect the "ecological validity" of performing that task; namely the natural, life-like manner in which the examinee performs it[15, 16].

As noted earlier, several methods have been developed for recording and subsequently evaluating the process by which an examinee performs grapho-motor tasks. These prior art methods are based on a variety of "pencil and paper" techniques for manually recording the observed process. References 14, 17 and 18 describe methods that use multiple colored pencils, lists or flowcharts. For example, each time the examinee copies an important element of a geometric pattern; the examiner gives him a different colored pencil or makes a mark in the list or flowchart.

Since the pace of performing grapho-motor tasks is usually fast and since manual notation is relatively time consuming and often erroneous[19, 20], these and similar recording methods fail to record all the features of the process by which an examinee performs such tasks[20]. Hence, some researchers opt to use video recording to document the how an examinee draws simple or complex figures[21]. Video recording is cumbersome, time consuming and does not resolve all the issues described above. In addition, the above-mentioned inherent shortcomings of the prior art recording methods and the absence of recording methods that overcome them make it very difficult to use statistical methods for correlating performance of subjects on tests with other cognitive abilities[14]. Consequently, the process by which an examinee performs grapho-motor tasks is rarely evaluated in clinical settings, such as hospitals.

It is pointed out that methods employing computer-based and multi-media methods for increasing the utility of psychological testing have been disclosed. See U.S. Pat. No. 5,961,332, U.S. Pat. No. 5,991,565 and U.S. Pat. No. 6,115,683. These methods, however, are not applicable for recording processes of performing grapho-motor tasks.

Other methods have been suggested whereby an examinee actually performs psychological tests on a graphic display of a computer-based system interface (e.g. monitors, touch screens): Representative disclosures are included in U.S. Pat. Nos. 5,211,564, 5,218,535, 5,326,270, 5,379,213, 5,565,316 and 6,030,226. Although such testing methods have considerable merit for testing the general population, they are not adequate for tests that require the use of a pencil and paper. In addition, they are not ecologically valid. U.S. Pat. No. 6,629,846 describes a method by which an examiner observes the examinee and the examiner clicks on buttons that appear on the screen of his computer and which relate to elements of complex figures or of multi-element tasks. The method of U.S. Pat. No. 6,629,846 allows for recording the process of copying well-defined discrete multi-element figures and makes it possible to score it in real time. However, the method of U.S. Pat. No. 6,629,846 cannot fully record drawing of curved configurations, e.g. drawing a face of a man, cursive letters, and many other pencil and paper tasks. Methods have also been disclosed for digitizing the drawing and writing of individuals using various input devices. See U.S. Pat. Nos. 6,703,570, and 6,300,580.

There is thus a need for, and it would be highly advantageous to have a method of recording and scoring the process of performing ecologically valid computerized psychological tests that include one or more grapho-motor tasks.

All references cited herein are included by reference for all purposes as if fully set forth herein.

The term "test" as used herein refers to a psychological test for assessment, training and remediation of grapho-motor abilities including one or more tasks performed by an examinee. The terms "test" and "task" are used herein interchangeably.

The term "pen" as use herein refers to an instrument used for writing and includes pencil, or stylus and is used as a conventional writing instrument although may include sensory apparatus and data transfer apparatus (e.g. cable) for transferring graphic information regarding motion, e.g. traces, of the pen along a writing surface.

The term "surface" or "writing surface" as used herein, includes conventional writing surfaces and may include sensory or storage apparatus for transferring or storing information regarding writing on the surface.

The term "examinee" as use herein refers to a subject that performs grapho-motor tasks for testing as well as for remediation and training.

REFERENCES (1) Rey, A. (1941). L'examen psychologie dan les cas d'encéphalopathie traumatique (Les problèmes). *Archives de Psychologie,* 28, 286-340.

(1) Critchley, M. (1953). *The parietal lobes.* Hafner Publ. Co., New York.

(2) Yerkes, R. M. (Ed.) (1921) Psychological examining in the United States Army. Memoirs of the National Academy of Sciences, 15, 1-890.

(3) Bender, L. (1938). A visual-motor gestalt test and its clinical use. American Orthopsychiatric Association Research Monographs, No. 3.

(4) Wechsler, D. A. (1945). A standardized memory scale for clinical use. Journal of Psychology, 19, 87-95.

(5) Gary Groth-Marnat (1990). Handbook of Psychological Assessment. John Wiley & Sons, Inc.

(6) Spreen O. & Strauss E., (1998). A Compendium of Neuropsychologica Tests. Oxford University Press, New York.

(7) Lezak, M. (1995). Neuropsychological Assessment. Oxford University Press, New York.

(8) Kaplan, E. (1988). A process approach to neuropsychological assessment. In T. Boll, & B. K. Bryant (Eds.), Clinical neuropsychology and brain function: Research, measurement, and practice (pp. 125-167). Washington, D.C.: American Psychological Association.

(9) Poreh, A. (2000). A quantitative evaluation of the copying process of the Rey Osterrieth Complex Figure. International Journal of Neuropsychological Assessment, 1, 1-10.

(10) Poreh, A. (2002). Neuropsychological Testing in the 21st Century. Editor of Special Issue. CNS Spectrums— The International Journal of Neuropsychiatric Medicine, 7, 340.

(11) Poreh, A. M. (2000). The quantified process approach: An emerging methodology to neuropsychological assessment. Clinical Neuropsychologist, 14(2), 212-222.

(12) Poreh A. (in press). Introduction to the Quantified Process Approach. In The Quantified Process Approach to Neuropsychological Assessment, Edited by Amir Poreh, to be published by Psychological Press: New York.

(13) Poreh A. (in press). Quandaries of the Quantified Process Approach. In The Quantified Process Approach to Neuropsychological Assessment, Edited by Amir Poreh, to be published by Psychological Press: New York.

(14) Standards for Educational and Psychological Testing: American Educational Research Association, February, 2000.

(15) Sbordone, R. J. and Long, C. J. Ecological Validity of Neuropsychological Testing (1996) Delray Beach, Fla.: GR Press/St. Lucie Press.

(16) Knight, J. A. (2003a). The Rey-Osterrieth Complex Figure: Overview of the handbook, current uses, and future directions. In J. A. Knight & E. Kaplan (Eds.), The handbook of Rey-Osterrieth Complex Figure usage: Clinical and research applications (pp. 5-25). Lutz, F L: Psychological Assessment Resources.

(17) Savage, C. R., Baer, L., Keuthen, N. J., Brown, H. D., Rauch, S. L., & Jenike, M. A. (1999). Organizational strategies mediate nonverbal memory impairment in obsessive-compulsive disorder. Biological Psychiatry, 45, 905-916.

(18) Charter, R. A., Waldrem K. D., and Padilla, S. P. (2000). Too many simple clerical scoring errors: The Rey Figure as an example. Journal of Clinical Psychology, Volume 56, Issue 4, 571-574.

(19) Jolliffe, T. & Baron-Cohen, S. (1997). Are people with autism and Asperger Syndrome faster than normal on the Embedded Figures Test? Journal of Child Psychology and Psychiatry, 1997, 38, 527-53.

(20) Stern, R. A., Javorsky, D. J., Singer, E. A., Harris, N. G. S., Somerville, J. A., Duke, L. M., Thompson, J. A., & Kaplan, E. (1999). BQSS: The Boston Qualitative Scoring System for the Rey-Osterrieth Complex Figure: Professional manual. Lutz, F L:

SUMMARY OF THE INVENTION

According to the present method there is provided a computerized method for administering, recording and scoring a psychological examination by an examiner to an examinee. During the psychological examination the examinee performs a grapho-motor task. A computer is attached to a storage device and a visual display attached to the computer is viewed by the examiner. The examinee is provided a pen and a writing surface. The pen includes a sensory mechanism operative to sense writing motion of the pen on the surface. The examinee performs the grapho-motor task, including the writing motion and the pen leaves a visible trace on the writing surface. The graphomotor task is recorded by collecting information into the storage device using the sensory mechanism. The collected information regards the performance of the grapho-motor task. Preferably, the recording includes digitizing the motion of the pen along the surface. Typically, a program is installed into the computer and the program enables the recording. Preferably, the information is presented to the examiner on the visual display either simultaneously with the recording, i.e. in real time, or subsequent to the recording i.e. not in real time or subsequent to completion of the recording. The information presented typically includes a time integrated visual representation of the pen motion over the surface. The examiner typically scores by marking the information as presented on the visual display. Often, reference information is further presented to the examiner and the reference information is previously stored in the storage device The reference information is compared with the visual representation for scoring at least a portion of the grapho-motor task. Preferably, the examiner upon viewing the presented information, scores the grapho-motor task. Preferably, a start time of the grapho-motor task is designated and an image is captured at a moment in time, the captured image is typically displayed on the visual display, the captured image being a time integrated representation the pen motion; A task time is recorded from the start time of the grapho-motor task and the captured image and the task time are stored in the storage device. Typically, the captured image is played by reading the captured image from the storage device and presented on the visual display according to the task time.

According to the present method there is provided a computerized method for administering, recording and scoring a psychological examination by an examiner to an examinee. During the psychological examination the examinee performs a grapho-motor task. A computer is attached to a storage device and a visual display attached to the computer is viewed by the examiner. The examinee is provided a pen and a writing surface. The pen includes a sensory mechanism operative to sense writing motion of the pen on the surface. The examinee performs the grapho-motor task, including the writing motion and the pen leaves a visible trace on the writing surface. The grapho-motor task is recorded by collecting information into the storage device using the sensory mechanism. An image is captured which is a time integrated representation of the pen motion and the captured image is displayed on the visual display either simultaneous or subsequent to the capture. The computer presents on the visual display at least one characteristic of the performance of the grapho-motor task. The examiner scores the characteristic of grapho-motor test by using an input device operatively attached to the computer to mark on the visual display.

According to the present invention there is provided a program storage device readable by a machine, tangibly embodying a program of instructions executable by the machine to perform a computerized method for administering a psychological examination by an examiner to an examinee, wherein during said psychological examination said examinee performs a grapho-motor task, the method described herein.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
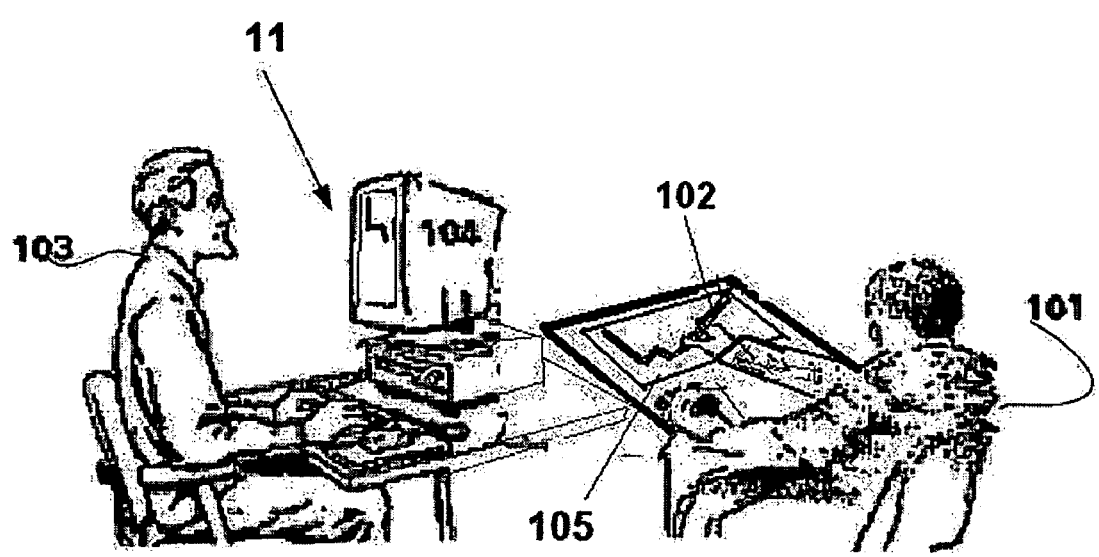
FIG. 1 is a drawing of an examiner testing an examinee performing a grapho-motor task, according to an embodiment of the present invention.

The present invention is of a system and method of performing, recording and scoring a computerized psychological test which includes one or more grapho-motor tasks. Specifically, the system and method includes the examinee holding a pen, e.g. a digital pen attached to the computer and digitizing the motion of the pen over a surface. The examiner controls the course of the examination and may play back the recorded response of the examinee at any time.

The principles and operation of a system and method of controlling and recording a grapho-motor task during a psychological examination, according to the present invention, may be better understood with reference to the drawings and the accompanying description.

Before explaining embodiments of the invention in detail, it is to be understood that the invention is not limited in its application to the details of design and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

By way of introduction, a principal intention of the present invention is to correctly and fully evaluate and assess a process of performing given grapho-motor tasks while maintaining ecological validity of the test. Hence, it is required to fully observe the tasks, taking into account order, speed and quality at which various parts of the tasks have been performed, to make a record of these observations, to assess them individually and, finally, to assess the final performance. Detailed requirements vary from task to task. In some cases, it is essential to assess the performance of an examinee on tests or training sessions in real time in order to reveal, as soon as possible, his deficiencies or difficulties, either for determining and carrying out immediately the required remediation action or for determining which additional tasks he should perform; in other cases it may be advantageous to perform the scoring at another convenient time. In many cases it is desired to have the capacity to review the observed process for reevaluation or for presenting the observed process to other experts or to courts in cases of litigation. In some cases it is desired to make a record of the performance up to a certain stage of the test. In some cases, the assessment or classification of the grapho-motor characteristics of an examinee is accomplished by comparing the shapes with examples of typical distorted copied shapes of figures associated with particular cognitive characteristics of examinees. As such examples are scattered in books and articles, such comparisons consume considerable time.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

The present invention uses a graphic input device, e.g. a digital pen functionally associated with a data storage device that preferably leaves a trace on the writing surface that is visible to the examinee. Any suitable data storage device that can be configured to communicate with a specific graphic input device can be used to implement embodiments of the present invention. However, according to embodiments of the present invention, it is most advantageous to use a computer-based device such as a desktop computer, portable computer or a personal digital assistant (PDA). A computer based device allows simple manipulation and storage of collected data, and immediate analysis and scoring of a given test. All communications between elements of the hardware may be accomplished using wireless methods.

Reference is now made to FIG. 1, which illustrates a method according to embodiments of the present invention. An examiner 103 asks examinee 101, after a short training session, to perform a required grapho-motor task on a writing surface using a digital pen 102 that leaves a trace on surface or pad 105. Such digital pens 102 are commercially available, e.g., the pens produced by Anoto (Anoto Group AB Stockholm, Sweden) or Pegasus (Pegasus Technologies LTD, Israel) and described by U.S. Pat. Nos. 6,703,570, and 6,300,580. U.S. Pat. Nos. 6,703,570, and 6,300,580 are incorporated herein by reference for all purposes as if entirely set forth herein. Pen 102 leaves a visual trace on writing surface 105 and the pen motion across surface 105 is digitized by sensing time-dependent positions of pen 102 on surface 105. The time dependent position is converted to digital data, which are transferred to a computer system 11 and stored in computer memory or storage preferably in real time. Alternatively, the data is buffered temporarily in storage attached to pen 102 or surface 105. Appropriate software installed in computer system 11. The software enables examiner 103 to view the time dependent trace on computer display 104 and records the trace in various ways using an input pointer device, e.g. a mouse or specific keys of a keyboard.

Figure 2:
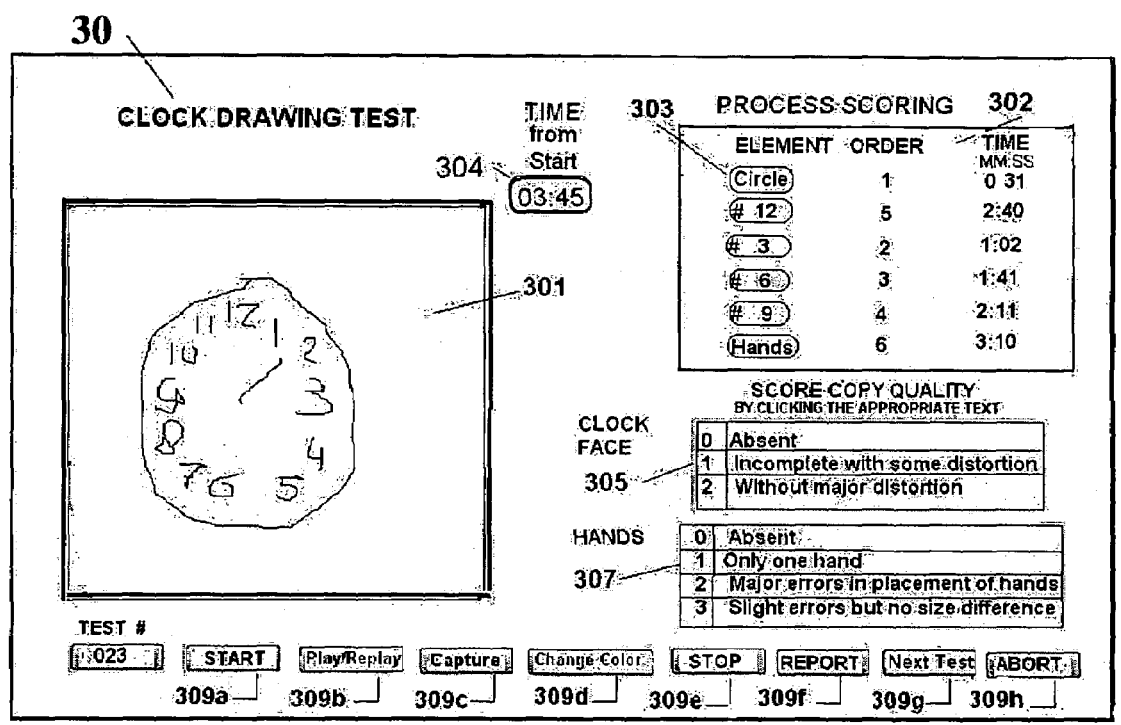
FIG. 2 is a drawing of a layout of a screen in a visual display of a computer programmed and running according to an embodiment of the present invention.

Reference is now made to FIG. 2, which schematically illustrates a screen layout 30 of the visual display 104 during a psychological examination according to an embodiment of the present invention in which examinee 101 is requested to draw a face of a clock. The shape of the drawing by examinee 101 at any time from the beginning of the test appears in view window 301. In this particular embodiment and illustration, the time, shown on the screen in digital clock 304, is 3:45 (min:sec)

Buttons 309 representing either virtual buttons on the display of 104 or alternatively real buttons on an input device, e.g. keyboard, are used by examiner 103 to initiate commands.

Typical commands are shown in the figure:

Button 309a defines and records the start of test, i.e. the start of performing the task by examinee 101. Time is then recorded from the start of the task and the time-dependent image of the trace is stored in a storage device of computer system 11.

Button 309b commands the computer to start presenting the trace of the drawing in view window 301. When examiner 103 is unclear about scoring the process or fails to fully record it, examiner 103 has an option at the end of the test to Replay the test (button 309b) causing the images as performed to be played again in viewing window 301 at a desired speed, and correct the scoring. Command 309b may be used to present the trace in real time or to present the trace subsequent to the current task by replaying at any desired later time.

Button 309c captures or performs "grabbing" of the image of the trace shown on display 104 at the time of capturing and thus shows an image of the trace on the writing surface 105 at the corresponding time from the beginning of the test. Note that capturing may be performed also during replay of the recorded time-dependent image. The capture command 309c will store that image as well as record in the storing device the capture time from the beginning of the test, so that the time dependent trace may be viewed later and may be included in a report describing the performance process. Captured images are thus typically time integrated portions of the motion of pen 102 over writing surface 105.

Button 309d changes the color or other image attribute at which the forthcoming part of the image of the trace produced by the digital pen will appear and be recorded.

Button 309e designates the end or stopping of the test.

Button 309f enters an administrative function useful for preparing a report.

Other commands (buttons 309 not shown) include numbering or otherwise classifying or marking the images. A series of images may be collected that describe the test process for future use. At the end of each grapho-motor task, the performance e.g. speed of performing each part of the task may be calculated.

In addition, the software installed in computer system 11 may be used to execute in a similar way appropriate administrative commands, such as recording information regarding examinee 101 in a desired format and presenting the information on visual display 104, recording the nature and date of the test and comments of examiner 103, presenting on visual display 104 instructions how to execute the test, and presenting on visual display 104 a time clock showing time from the start of the test 304. Similarly, scoring commands may be executed from visual display 104, e.g. a touch screen or keyboard, such as attaching scores for the quality of performance of parts of the task as defined by the grabbed images. When assessing or premeditating writing skills, images of various drawing modes and letters, for example, typically appear in a reference window on the screen. Thus, examiner 103 could easily compare the image in the view window with the images in the reference window and record, by clicking on the appropriate image, which mode of copying examinee 101 is using. In other cases a Yes/No type questionnaires appear in a dedicated window on screen 104, which examiner 103 may use to characterize the copying process by clicking or highlighting. In some cases, command buttons 309 for recording characteristics of the process will appear, such as for clockwise copying, and continuous or intermittent contact of pen 102 with paper or surface 105.

Check boxes 303 for scoring the process in this embodiment and test appear in window 302. Each time examiner 103 uses a check box 303 that corresponds to a particular element of the drawing, the performance time is recorded and subsequently presented in window 302 together with the order that the various elements were performed. Similarly, the virtual command text buttons 305 and 307 enable the examiner 103 to assess and record the quality of the drawing in real time or during a replay.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described with respect to a limited number of embodiments, it will be appreciated that many variations, modifications and other applications of the invention may be made.

What is claimed is:

1. A computerized method for administering, recording and scoring a psychological examination by an examiner to an examinee, wherein during said psychological examination said examinee performs a grapho-motor task, the method comprising:

(a) providing a storage device and a visual display operatively attached to a computer, wherein said visual display is viewed by the examiner and providing a pen and a writing surface, wherein said pen includes a sensory mechanism operative to sense writing motion of said pen on said writing surface, wherein said pen is operatively attached to said computer;

(b) the examinee performing said grapho-motor task, wherein said grapho-motor task includes said writing motion, wherein said performing includes said pen leaving a visible trace on said surface; and (c) recording the grapho-motor task by collecting information into said storage device using said sensory mechanism, said information regarding said performing, wherein the examiner scores a characteristic of said information by marking said visual display.

2. The method, according to claim 1, wherein said recording includes digitizing said motion of said pen along said surface.

3. The method, according to claim 1, further comprising the step of:
(d) installing a program in said computer, wherein said program enables said recording.

4. The method, according to claim 1, further comprising the step of:
(d) presenting to the examiner at least a portion of said information on said visual display.

5. The method, according to claim 4, wherein said presenting is simultaneous with said recording.

6. The method, according to claim 5, further comprising the step of:
(d) upon viewing said presenting, scoring by the examiner at least a portion of the grapho-motor task.

7. The method, according to claim 4, further comprising the step of:
(e) scoring by the examiner by marking at least at portion of said information as presented on said visual display.

8. The method, according to claim 4, wherein said presenting includes a time-integrated visual representation of said motion over said surface;
(e) further presenting to the examiner reference information previously stored in said storage device, wherein said reference information is compared with said visual representation for scoring at least a portion of the grapho-motor task.

9. The method, according to claim 1, further comprising the step of:
(d) designating a start time of the grapho-motor task; and
(e) capturing a captured image at a moment in time, wherein said captured image is a time integrated representation of at least a portion of said motion;
(f) recording a task time from said start time of the grapho-motor task; and
(g) storing said captured image and said task time in said storage device.

10. The method, according to claim 9, further comprising the steps of:
(h) playing said captured image by reading said captured image from said storage device and presenting said captured image according to said task time on said visual display.

11. A computerized method for administering, recording and scoring a psychological examination by an examiner to an examinee, wherein during said psychological examination said examinee performs a grapho-motor task, the method comprising:

(a) providing a storage device and a visual display operatively attached to a computer, wherein said visual display is viewed by the examiner and providing a pen and a writing surface, wherein said pen includes a sensory mechanism operative to sense writing motion of said pen on said writing surface, wherein said pen is operatively attached to said computer;

(b) the examinee performing said grapho-motor task, wherein said grapho-motor task includes said writing motion, wherein said performing includes said pen leaving a visible trace on said surface; and (c) recording the grapho-motor task by collecting information into said storage device using said sensory mechanism, said information regarding said performing;

(d) capturing an image at a moment in time, thereby producing a captured image, displaying said captured image on said visual display, wherein said captured image is a time integrated representation of at least a portion of said motion;

(e) presenting by the computer on the visual display at least one characteristic of said performing; and (f) the examiner scoring said characteristic by using an input device operatively the computer to mark said visual display.

12. A program storage device readable by a machine, tangibly embodying a program of instructions executable by the machine to perform a computerized method for administering a psychological examination by an examiner to an examinee, wherein during said psychological examination said examinee performs a grapho-motor task, the method comprising the steps of:

(a) providing a storage device and a visual display operatively attached to a computer, wherein said visual display is viewed by the examiner and providing a pen and a writing surface, wherein said pen includes a sensory mechanism operative to sense writing motion of said pen on said writing surface, wherein said pen is operatively attached to said computer;

(b) the examinee performing said grapho-motor task, wherein said grapho-motor task includes said writing motion, wherein said performing includes said pen leaving a visible trace on said surface; and (c) recording the grapho-motor task by collecting information into said storage device using said sensory mechanism, said information regarding said performing.

13. A program storage device readable by a machine, tangibly embodying a program of instructions executable by the machine to perform a computerized method for administering a psychological examination by an examiner to an examinee, wherein during said psychological examination said examinee performs a grapho-motor task, the method comprising the steps of claim 12.

* * * * *